United States Patent [19]

Carli

[11] Patent Number: 4,639,370

[45] Date of Patent: Jan. 27, 1987

[54] PHARMACEUTICAL COMPOSITION

[75] Inventor: Fabio Carli, Turin, Italy

[73] Assignee: Farmitalia Carlo Erba S.p.A., Milan, Italy

[21] Appl. No.: 698,815

[22] Filed: Feb. 6, 1985

[30] Foreign Application Priority Data

Feb. 8, 1984 [GB] United Kingdom ................. 8403359

[51] Int. Cl.$^4$ ............................................. A61K 31/79
[52] U.S. Cl. ..................................................... 424/80
[58] Field of Search ..................................... 424/78, 80

[56] References Cited

U.S. PATENT DOCUMENTS 4,482,534 11/1984 Blank .................................... 424/80
4,555,399 11/1985 Hsiao .................................... 424/80

Primary Examiner—Elbert L. Roberts
Attorney, Agent, or Firm—Oblon, Fisher, Spivak, McClelland & Maier

[57] ABSTRACT

A water-swellable, water-insoluble polymer is loaded with a biologically active substance or substance convertible into a biologically active substance in vivo by preparing and grinding a mixture of a said substance with a water-swellable, water-insoluble polymer in a weight ratio of the said substance:polymer of from 1:0.1 to 1:100. The thus-loaded polymer is useful as a pharmaceutical composition.

7 Claims, No Drawings

PHARMACEUTICAL COMPOSITION

BACKGROUND OF THE INVENTION

1. Field of the Invention

The present invention relates to a method of preparing formulations comprising a biologically active substrate or substance which is converted into a biologically substance.

2. Description of the Prior Art

The wettability and dissolution properties of a biologically active substance or substance which is converted thereinto in vivo such as a drug or drug precursor greatly influence the bioavailability of the drug or drug precursor. In many cases, very active drugs or drug precursors, for example, present a poor absorption profile because of their unfavourable dissolution characteristics. Such techniques as reducing the particle size of the drug and the addition of wetting agents have been widely appplied to obviate these problems. However, these techniques frequently prove to be not effective enough. Therefore much effort has been devoted to develop new formulations or new techniques to achieve better results. Considerable experimental work in this area has recently opened up two new research lines based on the preparation of "solid dispersions" and of "inclusion compounds". In the former approach the drug or drug precursor is molecularly dispersed in the carrier, usually a water-soluble polymer (S. Riegelman, W. L. Chiou 987,588 4/1976 Canada), while in the latter approach the drug or drug precursor forms molecular complexes with water-soluble cyclodextrins (J. Szejtli "Cyclodextrins and Their Inclusions Compounds", Akademia Viado, Budapest 1982). A need therefore continues to exist for a method and formulations by which the bioavailability of a biologically active substance or a substance convertible into a biologically active substance in vivo can be improved.

SUMMARY OF THE INVENTION

Accordingly, one object of the present invention is to provide a biologically active substance or a substance convertible into a biologically active substance in vivo in a formulation which increases the bioavailability of the drug.

Briefly, this object and other objects of the present invention as hereinafter will become more readily apparent can be attained by a process for loading a water-swellable, water-insoluble polymer with a biologically active substance or a substance convertible into a biologically active substance in vivo by preparing and grinding a mixture of said substance with a water-swellable, water-insoluble polymer in a weight ratio of the said substance: polymer of from 1:0.1 to 1:100.

The present invention also provides a polymer formulation of a biologically active substance or a substance convertible into a biologically active substance in vivo in weight ratio of said substance to polymer of from 1:0.1 to 1:100.

DETAILED DESCRIPTION OF THE PREFERRED EMBODIMENTS

A remarkable enhancement of the dissolution and bioavailability of poorly water-soluble substances can be achieved in the present invention, particularly if the drug or drug precursor has physico-chemical characteristics which are unfavourable (poor wettability, poor dissolution characteristics in aqueous media) to its in vivo absorption. The discovery of the present invention is that grinding of the drug or drug precursor with swellable, water-insoluble polymers improves the stated characteristics and, consequently, the bioavailability of the drug.

The cogrinding technique of the present invention brings about the following effects:

1. An increase of the wettability of the drug or drug precursor as a consequence of the very large dispersion of it in and on the network of the highly hydrophilic and swellable polymer.

2. An increase of solubility of the drug or drug precursor caused by a complete or partial transition of the original crystalline network of the drug or drug precursor to a higher energy (lower melting point) structure and/or to a complete or partially amorphous form.

In addition to the above specified advantages, the drug or drug precursor loaded on at least one water-swellable, water-insoluble polymer may also present other improved physicochemical or technological properties.

The biologically active substance or substance which is converted thereinto in vivo is preferably a drug or drug precursor. For convenience hereinafter drugs and drug precursor will be referred to collectively as "drugs", with reference to which the present invention is described by way of example below.

The basic advantages of the drug/polymer systems obtained by the process of the present invention are:

1. A remarkable increase of the drug wettability because of the high hydrophilicity and swelling capacity in water of the hydrophilic, swellable, water-insoluble polymers.

2. A rapid swelling and disintegration in water of the system and immediate dispersion of the drugs. Some of the hydrophilic, swellable, water-insoluble polymers which may be used in the present process are, in fact, already used and marketed as disintegrants for oral solid dosage forms.

3. Avoidance of the viscous layer around the drug which can be related with the use of water-soluble polymers and which can hinder the drug diffusion and slow down the dissolution process.

In addition, loading of drugs in and on swellable water-insoluble polymers by the cogrinding technique presents advantages over the loading method based on swelling of the polymer in an organic solvent containing the drug (B. C. Lippold et al., D.O.S., No. 2,634,004).

The basic advantages of the cogrinding technique over the swelling method are:

1. The avoidance of all the problems of toxicity and inflammability related to the use of solvents.

2. The possibility of loading larger quantities of drug in and on the swellable polymer. In fact, the maximum amount of drug which can be loaded by the solvent swelling method is limited both by the swelling volume and the solubility of the drug in that solvent.

3. At the same drug swellable polymer ratio, better dissolution rates and also better bioavailability can be achieved by the ground mixture compared to the solvent loaded mixture, as the grinding technique increases also the surface area of the resulting product.

4. At low drug swellable polymer ratios, better dissolution and consequently also better bioavailability can be achieved by the ground mixture in comparison to the solvent loaded mixture, since the grinding technique can lead to a higher degree of amorphization.

The present invention involves the grinding of a mixture of an active drug and any water-insoluble hydrophilic, swellable polymer or combinations of two or more polymers. Suitable examples of such polymers are: (a) cross-linked polyvinylpyrrolidone (National Formulary XV, Supplement 3, pag. 368), hereinafter abbreviated as cross-linked PVP, (b) cross-linked sodium carboxymethylcellulose (National Formulary XV, Supplement 3, pag. 367), (c) cross-linked dextran and the like. The common characteristics of these polymers are:

1. High swelling ability in water (from 0.1 ml to 100 ml of water volume uptake per gram of dry polymer). This characteristic brings about a high degree of swelling and an effective disintegration in water or in biological fluids of the systems with a powerful dispersion of its constitutents and an immediate release of the drug molecules.

2. A fast rate of water swelling e.g. cross-linked PVP achieves maximum swelling in less than five minutes. This property means that the aforementioned effects of swelling, disintegration, dispersion and dissolution of the drug molecules can be accomplished in a very short period of time.

3. Water insolubility: This property rules out possible negative effects which are able to slow down the drug dissolution process, e.g. by building up a viscous layer around the drug, and brings about the formation of a finely dispersed suspension which assures a rapid gastric emptying to the absorption site.

The basic procedure of the grinding technique of the invention of a mixture of an active drug and at least one water-swellable, water-insoluble polymer occurs as follows: A simple dry physical mixture of the drug and at least one of the swellable, insoluble polymers mentioned supra is placed in a rotating ball mill, in a vibrational ball mill, in an automatic mortar mill or any other suitable crushing apparatus and ground until complete amorphization of the crystalline drug is achieved.

The completeness of the amorphization process can be checked by the absence in the Differential Scanning Calorimetry thermogram of the resulting drug-polymer system of the transition peak relative to the solid/liquid endothermic transition of the crystalline drug. The absence of the transition peak means that the enthalpy of melting is practically zero.

The grinding of the drug-swellable polymer mixture can also be stopped any time ranging from 0–100% of drug amorphization, as measured by the reduction of the enthalpy of melting of the crystalline drug, so long as sufficient amorphization has occurred to sensibly increase the dissolution rate. Alternatively, the grinding of the drug-swellable polymer mixture can be stopped any time the original crystalline form of the drug has been transformed into another, more energetic form. This transformation is indicated by the shifting of the original endothermic peak of the DSC thermogram to lower temperatures, which leads to higher dissolution rates and bioavailability.

The weight ratios between the drug and the swellable insoluble polymer in the mixture to be ground can vary from 1:0.1 to 1:100 w.w. of drug:polymer, preferably from 1:1 to 1:100 w.w. drug:polymer. For each drug:polymer weight ratio composition and for each total amount of mixture the correct time of grinding necessary for the desired degree of amorphization or for the formation of a higher energy form of the drug must be checked. Therefore, for each drug:polymer system the most practical combination of weight ratio and time of grinding can be identified. Examples of drug:swellable insoluble polymer weight ratios and grinding times will be given later.

The resulting ground mixture of the active drug and the swellable insoluble polymer can then be forced through a sieve to eliminate possible aggregates and subsequently mixed in any mixing device to warrant further homogeneity. The resulting powdered ground system of the drug and the swellable polymer can be subsequently used to prepare any desired dosage form such as capsules, tablets, and the like, with or without the addition of any of the common excipients used in pharmaceutical formulations.

Any active drug with water poor dissolution characteristics can be treated by the swellable polymer co-grinding technique described by the present invention. Suitable examples of drugs include: slightly soluble steroid hormones such as progesterone, hydrocortisone, prednisolone, and the like; non-steroidal hormones such as dienesterol, diethylstylbene sterol dipropionate, and the like; antibiotics such as chloramphenicol, chloramphenicol palmitate, erythromycin, griseofulvin, nystatin, and the like; anti-inflammatory drugs such as indomethacin, indoprofen, ketoprofen, flufenamic acid, and the like; sedative drugs such assphenobarbital, diazepam, and the like; drugs of any other class of pharmacological activity which present poor dissolution properties. The amount of the polymer/drug system of the present invention which is administered to a subject will depend upon a variety of factors including the drug employed, the condition to be treated and the age and condition of the patient.

Having generally described the invention, a further understanding can be obtained by reference to certain specific examples which are provided herein for purposes of illustration only and are not intended to be limiting unless otherwise specified.

EXAMPLE 1

A 2 gram amount of crystalline medroxyprogesterone acetate (a synthetic steroid, with antiestrogenic activity at low doses, and with anti-cancer activity at high doses) and 6 grams of cross-linked PVP were mixed with a suitable mixer, subsequently placed in an automatic mortar mill and ground for three hours. The resulting medroxyprogesterone acetate/cross-linked PVP powdered system was then sieved to 260 $\mu$m range and subsequently mixed with a suitable mixer. This powdered medroxyprogesterone acetate/cross-linked PVP system could then be made into any desired dosage form.

EXAMPLE 2

The medroxyprogesterone acetate/cross-linked PVP (1:3 w/w) system described in Example 1 was employed to prepare tablets having the following unitary composition:

medroxyprogesterone acetate/cross-linked PVP (1:3 w/w) system: 200 mg cross-linked PVP: 40 mg in which pure cross-linked PVP is added only as a disintegrating agent. The aforementioned ingredients were thoroughly mixed with a suitable mixer and subsequently compressed to tablets with a 13 mm flat punch compaction machine.

EXAMPLE 3

A 2 gram amount of crystalline medroxyprogesterone acetate and 6 grams of cross-linked PVP were mixed in a suitable mixer, subsequently placed in an automatic mortar mill and ground for eight hours. The resulting medroxyprogesterone acetate/cross-linked PVP system was then sieved to 260 μm range and subsequently mixed with a suitable mixer.

This powdered medroxyprogesterone acetate/cross-linked PVP system could then be made into any desired dosage form.

EXAMPLE 4

A 1 gram amount of indoprofen and 3 grams of cross-linked PVP were mixed in a suitable mixer, subsequently placed in an automatic mortar mill and ground for three hours. The resulting indoprofen/cross-linked PVP system was then sieved to 260 μm range and subsequently mixed with a suitable mixer. This powdered indoprofen/cross-linked PVP system could then be made into any desired dosage form.

EXAMPLE 5

A 1 gram amount of griseofulvin and 3 grams of cross-linked PVP were mixed in a suitable mixer, subsequently placed in an automatic mortar mill and ground for three hours. The resulting griseofulvin/cross-linked PVP system was then sieved to 260 μm range and subsequently mixed with a suitable mixer. This powdered griseofulvin/cross-linked PVP system could then be made into any desired dosage form.

EXAMPLE 6

A 1 gram amount of griseofulvin and 3 grams of cross-linked PVP were mixed in a suitable mixer, subsequently placed in an automatic mortar mill and ground for six hours. The resulting griseofulvin/cross-linked PVP system was then sieved to 260 μm range and subsequently mixed with a suitable mixer. This powdered griseofulvin/cross-linked PVP system could then be incorporated into any desired dosage form.

EXAMPLE 7

A 1 gram amount of griseofulvin and 10 grams of cross-linked PVP were mixed in a suitable mixer, subsequently placed in an automatic mortar mill and ground for six hours. The resulting griseofulvin/cross-linked PVP system was then sieved to 260 μm range and subsequently mixed with a suitable mixer. This powdered griseofulvin/cross-linked PVP system could then be made into any desired dosage form.

EXAMPLE 8

A 1.25 gram amount of indomethacin and 3.75 grams of cross-linked sodium carboxymethylcellulose were mixed in a suitable mixer, subsequently placed in an automatic mortar mill and ground for 5 hours. The resulting indomethacin/cross-linked sodium carboxymethylcellulose system was then sieved to 260 μm range and subsequently mixed with a suitable mixer. This powdered indomethacin/cross-linked sodium carboxymethylcellulose system could then be made into any desired dosage form.

Differential Scanning Calorimetry Data

The D.S.C. (TA 3000, Mettler) data relative to the preparations obtained by grinding medroxyprogesterone acetate with polymer as described in Examples 1 and 3, are presented in Table 1. In the case of the ground mixture (1:3 w/w) of MAP and cross-linked PVP, at three hours of grinding there is a ~60% reduction of the heat of fusion and the transformation of the original crystalline state (205.6° melting point) into a higher energy form (196° melting point). After eight hours of grinding the heat of fusion reduction is increased up to more than 90% and the residual crystallinity is due to an even higher energy form (162° melting point). The D.S.C. data relative to the preparation containing indoprofen, described in Example 4, are shown in Table 2. After three hours of cogrinding, practically a complete amorphization of the original crystalline indoprofen is obtained. In Table 3, the D.S.C. data relative to the griseofulvin ground systems are shown. In the case of the mixture with the cross-linked PVP, for the weight ratio 1:3, after three hours of grinding there is a 60% reduction of the heat of fusion, whereas after six hours there is a 90% reduction. If the weight ratio is 1:10 at six hours of grinding time, there is a complete amorphization. In Table 4, the D.S.C. data relative to the indomethacin ground mixture are reported. After five hours of grinding, the 1:3 w/w mixture of indomethacin and cross-linked sodium carboxymethylcellulose presented an 85% reduction of the original heat of fusion and the shifting of the melting point to a lower value.

Solubility Data (A) Medroxyprogesterone acetate/swellable polymer ground mixture.

The solubility of the MAP/swellable polymer ground mixture described in Example 1 was assessed by placing an excess amount of the powder, equivalent to 50 mg of MAP, in flasks containing 50 ml of pH 5.5 buffer solution, at 37° C. The flasks were placed in a shaking thermostated apparatus and aliquots of sample solutions were taken by filtering through a Millipore membrane. The concentration of MAP in the filtered aliquot was determined both by spectrophotometry (SP 8-100, Pye Unicam) after dilution with methanol, $\lambda = 247$ nm, and by HPLC (column: Spherisorb S30 D52, Phase Sep.; mobile phase acetonitrile/water 70/30 v/v; flow rate 1 ml/min; U.V. detection, $\lambda = 242$ nm), after dilution with acetonitrile. The solubility data of the MAP/cross-linked PVP (1:3 w/w) ground mixture described in Example 1 are reported in Table 5.

To demonstrate the unique properties of the cogrinding technique, Table 5 also contains the solubility data of pure crystalline MAP, of the physical mixture of MAP and cross-linked PVP and of the MAP/cross-linked PVP system prepared by solvent swelling (4 ml of a 50 mg/ml methylenechloride solution of MAP over 1 gram of cross-linked PVP). It is possible to observe that in the case of the ground mixture prepared by the method described by the present invention the MAP dissolved at the different times is higher than in the case of the pure MAP or of the physical mixture of MAP and swellable polymer. It is also interesting to observe that the cogrinding technique of this invention originates MAP concentrations also higher than the concentrations originated by the MAP/swellable polymer system prepared by the solvent swelling method (4 ml of 50.0 mg/ml methylenechloride solution of MAP over 1 g of cross-linked PVP).

(B) Indoprofen/swellable polymer ground mixture

The solubility of the indoprofen/cross-linked PVP ground mixture described in Example 4 was measured by following the procedure used for the MAP systems and a pH 2.0 buffer solution. The indoprofen concentrations were determined by spectrophotometry ($\lambda=280$ nm). As shown in Table 6, the ground mixture prepared by the method of the present invention originates indoprofen concentrations very much higher than the pure indoprofen or the physical mixture of indoprofen and swellable polymer. Furthermore, the ground system originates indoprofen concentrations at least as high as originated by the system prepared by the solvent swelling method (2.5 ml of 100 mg/ml dimethylformamide solution of indoprofen over 1 g of cross-linked PVP), but with the advantage that a lower polymer:drug ratio is necessary (3:1 VS 4:1).

(C) Griseofulvin/swellable polymer ground mixture

The solubility of the griseofulvin/cross-linked PVP ground mixtures described in Examples 5, 6, 7 was measured by following the procedure previously described and a pH 7.4 buffer solution. The griseofulvin concentrations were determined by spectrophotometry ($\lambda=294$ nm). As shown in Table 7, the ground mixtures prepared by the method described by the present invention originate griseofulvin concentrations very much higher than the pure griseofulvin or the physical mixture of griseofulvin and cross-linked PVP. Furthermore, the ground mixture solubility data are also higher than the griseofulvin concentrations originated by the system prepared by the solvent swelling method (4 ml of 83.3 mg/ml dimethylformamide solution of griseofulvin over 1 gram of cross-linked PVP).

(D) Indomethacin/swellable polymer ground mixture.

The solubility of the indomethacin/cross-linked sodium carboxymethylcellulose ground mixture described in Example 8 was measured by following the procedure previously described and a pH 6.8 buffer solution. The indomethacin concentrations were determined by spectrophotometry ($\lambda=317$ nm). As shown in Table 8, the ground mixture prepared by the method described by the present invention originates indomethacin concentrations not only higher than the pure indomethacin or the physical mixture of the drug and cross-linked sodium carboxymethylcellulose, but also higher than the 1:10 w/w system prepared by the solvent swelling method (1 ml of 100 mg/ml acetone solution of indomethacin over 1 gram of cross-linked sodium carboxymethylcellulose).

Bioavailability of Drug/Swellable Polymer Ground Mixtures

To provide the ability of the cogrinding technique in the present invention to improve the "in vivo" absorption of slightly soluble drugs, medroxyprogesterone acetate/cross-linked PVP (1:3 w/w) ground mixture was administered orally by the cross-over design described in Examples 2 to 6 to fasted beagle dogs (male and female, 9-13 kg of weight). The animals were not fed for 17 hours before the administration and for 4 hours after treatment. At predetermined times 4 ml blood samples were taken and transferred into heparinized tubes, centrifuged at 3000 r.p.m. for 10 minutes. The separated plasma was stored frozen ($-20°$ C.) until analysis. The MAP plasma levels were determined by a specific, accurate and precise method which consists of: extraction of MAP with n-hexane, clean-up of the extract (partition with acetonitrile), high performance liquid chromatographic separation (column: Lichrosorb RP 18 Merck; mobile phase:methanol:water, 75:25 v/v; flow rate; 1 ml/min; UV detection, at $\lambda=242$ nm). In Table 9 MAP plasma concentrations relative to tablets of the medroxyprogesterone acetate/cross-linked PVP (1:3 w/w) ground mixture described in Example 2 are presented. Control tablets were also administered, containing a physical mixture (1:3 w/w) of medroxyprogesterone acetate and cross-linked PVP, both ground separately for 3 hours. There is a dramatic increase of medroxyprogesterone acetate plasma concentrations following administration of the coground mixture prepared by the technique of the present invention. Drug plasma levels very much higher than control tablets are obtained. Also the AUC (area under the plasma drug concentration-time curve) values were remarkably higher in the case of the medroxyprogesterone acetate/swellable polymer coground system. Such "in vivo" data demonstrate the unique property of the drug/swellable polymer cogrinding technique of the present invention compared to the simple mixing of separately ground drug and swellable polymer.

In another bioavailability study, both the medroxyprogesterone acetate/cross-linked PVP coground mixture of Example 2 and a system of medroxyprogesterone acetate/cross-linked PVP prepared by the solvent swelling method were administered to six fasted beagle dogs. In this case the control tablets were commercial tablets containing 250 mg of crystalline medroxyprogesterone acetate. The resulting drug plasma concentrations are presented in Table 10. It is evident that both the systems prepared by the cogrinding technique and the solvent technique, although adminstered in a five times lower dose, originate drug plasma concentrations comparable or even higher than the commercial tablets. But it is also important to observe that the drug/swellable polymer mixture prepared by the cogrinding technique of the present invention originates drug plasma concentrations and also AUC values remarkably higher than the drug/swellable polymer system prepared by the solvent swelling method.

On the basis of both the "in vitro" and "in vivo" data previously presented, it is possible to conclude that the unique ability of the cogrinding technique of the present invention to enhance the dissolution and the bioavailability of drugs of low solubility has been demonstrated.

TABLE 1

Differential Scanning Calorimetry Data of Different Medroxyprogesterone acetate (MAP)/Swellable Polymer Ground Mixtures.

| System | Melting Point °C. | Heat of Fusion J/g | % Residual of Original Heat of Fusion |
|---|---|---|---|
| Pure crystalline MAP | 205-206 | 88.0 | 100.0 |
| MAP/cross-linked PVP 1:3 w/w (grinding method, 3 hrs) Example 1 | 195.9 | 33.1 | 37.7 |
| MAP/cross-linked PVP 1:3 w/w (grinding method, 8 hrs) Example 3 | 162.3 | 8.0 | 9.0 |

TABLE 2

Differential Scanning Calorimetry Data of Indoprofen/Swellable Polymer Ground Mixture.

| System | Melting Point °C. | Heat of Fusion J/g | % Residual of Original Heat of Fusion |
|---|---|---|---|
| Pure crystalline Indoprofen | 212-215 | 134.6 | 100.0 |
| Indoprofen/cross-linked PVP 1:3 w/w | 215.6 | 2.7 | 2.0 |

TABLE 2-continued

Differential Scanning Calorimetry Data of Indoprofen/Swellable Polymer Ground Mixture.

| System | Melting Point °C. | Heat of Fusion J/g | % Residual of Original Heat of Fusion |
|---|---|---|---|
| (grinding method, 3 hrs) Example 4 | | | |

TABLE 3

Differential Scanning Calorimetry Data of Different Griseofulvin/Swellable Polymer Ground Mixtures.

| System | Melting Point °C. | Heat of Fusion J/g | % Residual of Original Heat of Fusion |
|---|---|---|---|
| Pure crystalline Griseofulvin | 218.8 | 119.22 | 100 |
| Griseofulvin/cross-linked PVP 1:3 w/w (grinding method, 3 hrs) Example 5 | 183.4 | 47.37 | 39.7 |
| Griseofulvin/cross-linked PVP 1:3 w/w (grinding method, 6 hrs) Example 6 | 178.7 | 12.3 | 10.2 |
| Griseofulvin/cross-linked PVP 1:10 w/w (grinding method, 6 hrs) Example 7 | — | 0 | 0 |

TABLE 4

Differential Scanning Calorimetry Data of Indomethacin/Swellable Polymer Ground Mixture.

| System | Melting Point °C. | Heat of Fusion J/g | % Residual of Original Heat of Fusion |
|---|---|---|---|
| Pure crystalline Indomethacin | 160.2 | 110.8 | — |
| Indomethacin/cross-linked Sodium Carboxy-methylcellulose 1:3 w/w (grinding method, 5 hrs) Example 8 | 150.5 | 16.1 | 14.4 |

TABLE 5

Solubility Data (mcg/ml) of Medroxyprogesterone Acetate (MAP)/Swellable Polymer Ground Mixture (pH 5.5 phosphate buffer solution, 37° C.).

| MAP System | 5 min | 15 min | 1 hr | 6 hrs |
|---|---|---|---|---|
| Pure crystalline MAP | <0.04 | 0.32 | 0.68 | 1.00 |
| Physical mixture 1:3 w/w MAP/cross-linked PVP | 0.85 | 1.18 | 1.34 | 1.21 |
| MAP/crossed-linked PVP 1:5 w/w (by CH$_2$Cl$_2$ Swelling) | 1.00 | 1.61 | 1.69 | 2.04 |
| MAP/cross-linked PVP 1:3 w/w (grinding method, 3 hrs) Example 1 | 2.26 | 3.08 | 2.90 | 5.28 |

TABLE 6

Solubility Data (mcg/ml) of Indoprofen/Swellable Polymer Ground Mixture (pH 2.0 buffer solution, 37° C.).

| System | 5 min | 15 min | 1 hr | 3 hrs | 24 hrs |
|---|---|---|---|---|---|
| Pure crystalline Indoprofen | 1.6 | 3.0 | 4.8 | | 10.3 |
| Physical mixture 1:3 w/w Indoprofen:cross-linked PVP | 8.3 | 8.2 | 9.6 | 10.2 | 11.3 |
| Indoprofen/cross-linked PVP 1:3 w/w (grinding method, 3 hrs) Example 4 | 18.0 | 19.3 | 18.8 | 18.6 | 17.4 |
| Indoprofen/cross-linked PVP 1:4 w/w (solvent swelling method) | 19.3 | 16.8 | 15.7 | 14.6 | 14.8 |

TABLE 7

Solubility Data (mcg/ml) of Griseofulvin/Swellable Polymer Ground Mixture (pH 7.4, buffer solution, 37° C.).

| System | 5 min | 15 min | 1 hr | 3 hrs | 24 hrs |
|---|---|---|---|---|---|
| Pure crystalline Griseofulvin | 9.1 | 11.0 | 10.9 | 11.3 | 14.9 |
| Physical mixture 1:3 w/w Griseofulvin/cross-linked PVP | 18.9 | 19.3 | 21.2 | 23.9 | — |
| Griseofulvin/cross-linked PVP 1:3 w/w (grinding method, 3 hrs) Example 5 | 27.7 | 29.3 | 30.4 | 31.3 | 27.7 |
| Griseofulvin/cross-linked PVP 1:3 w/w (grinding method, 6 hrs) Example 6 | 29.8 | 39.7 | 33.8 | 34.2 | — |
| Griseofulvin/cross-linked PVP 1:10 w/w (grinding method, 6 hrs) Example 7 | 33.7 | 33.5 | 37.4 | 31.3 | 28.6 |
| Griseofulvin/cross-linked PVP 1:3 w/w (by solvent swelling) | 24.7 | 24.2 | 24.0 | 19.9 | 19.1 |
| Griseofulvin/cross-linked PVP 1:10 w/w (Physical mixture) | 11.2 | 11.8 | 15.5 | 14.4 | — |

TABLE 8

Solubility Data (mcg/ml) of Indomethacin Swellable Polymer Ground Mixture (pH 6.8 buffer solution, 37° C.).

| System | 5 min | 15 min | 1 hr | 3 hrs | 24 hrs |
|---|---|---|---|---|---|
| Pure crystalline Indomethacin | 230.2 | 358.2 | 482.1 | 502.8 | 502.0 |
| Physical mixture 1:10 w/w Indomethacin/cross-linked Sodium Carboxy-methylcellulose | 255.9 | 347.4 | 463.4 | 520.5 | 536.1 |
| Indomethacin/cross-linked Sodium Carboxy-methylcellulose 1:3 w/w (grinding method, 5 hrs) Example 8 | 817.8 | 867.7 | 773.9 | 757.0 | 744.0 |

TABLE 8-continued

Solubility Data (mcg/ml) of Indomethacin Swellable Polymer Ground Mixture (pH 6.8 buffer solution, 37° C.).

| System | Time | | | | |
|---|---|---|---|---|---|
| | 5 min | 15 min | 1 hr | 3 hrs | 24 hrs |
| Indomethacin/cross-linked Sodium Carboxymethylcellulose 1:10 w/w (solvent swelling method) | 284.9 | 337.1 | 401.1 | 419.2 | 408.6 |

TABLE 9

Plasma MAP Concentrations (ng/ml) Determined by HPLC Method from Bioavailability Studies in Fasted Beagle Dogs. (Means values and standard errors).

| | Preparation | |
|---|---|---|
| Time (hours) | Control Tablet[a] (Physical Mixture 1:3 w/w ground MAP ground cross-linked PVP) Mean of five dogs 2 × 50 mg | MAP/cross-linked PVP[b] 1:3 w/w (by cogrinding) Mean of six dogs 2 × 50 mg |
| 1 | 9.71 (3.91) | 86.67 (41.81) |
| 2 | 13.24 (6.62) | 95.99 (29.41) |
| 4 | 31.19 (14.30) | 79.58 (44.58) |
| 7 | 11.01 (2.80) | 25.41 (9.10) |
| AUC[c] (0-7 hrs) mcg × hr/ml | 123.57 (35.45) | 467.7 (150.11) |

[a]Control tablets unitary composition was as follows: 200 mg of physical mixture 1:3 w/w of MAP and cross-linked PVP alone as disintegrant. Each dog was given two tablets each containing 50 mg of MAP.
[b]Tablets of MAP/cross-linked PVP system were prepared as shown in Example 2. Each dog was given two tablets each containing 50 mg of MAP.
[c]Area under the plasma MAP concentration-time curve.

TABLE 10

Plasma MAP concentrations (ng/ml) Determined by HPLC Method from Bioavailability Studies in Fasted Beagle Dogs (Mean values and standard errors relative to six dogs).

| | Preparation | | |
|---|---|---|---|
| Time (hrs) | Commercial[a] Tablet 1 × 250 mg | MAP/Cross-linked PVP[b] 1:5 w/w System (solvent swelling method) 1 × 50 mg | MAP/cross-linked PVP[c] 1:3 w/w System (cogrinding method) 1 × 50 mg |
| 1 | 12.94 (2.80) | 23.48 (5.50) | 94.65 (39.56) |
| 2 | 20.33 (7.49) | 41.38 (13.62) | 69.21 (19.93) |
| 4 | 26.73 (18.48) | 16.06 (4.87) | 34.96 (15.45) |
| 7 | 9.51 (2.94) | 8.52 (2.51) | 11.63 (2.73) |
| AUC[d] (0-7 hrs) mcg × hr/ml | 124.5 (48.1) | 138.50 (32.30) | 303.31 (83.52) |

[a]Commercial tablet unitary composition was as follows: 250 mg of crystalline MAP; 121.25 mg of lactose; 60.00 mg of corn starch; 22.50 mg of linear polyvinylpyrrolidone; 31.25 mg of sodium carboxymethyl starch; 5 mg of magnesium stearate.
[b]Tablets composition was as follows: 300 mg of the system MAP/cross-linked PVP (1:5 w/w) prepared by the solvent swelling method.
[c]Tablets were prepared as shown in Example 2.
[d]Area under the plasma MAP concentration-time curve.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for loading a water-swellable, water-insoluble polymer with a biologically active substance or a substance convertible into a biologically active substance in vivo, which process comprises:
   preparing and grinding a mixture of a said substance with a water-swellable, water-insoluble polymer in a weight ratio of the said substance:polymer of from 1:0.1 to 1:100.

2. The process according to claim 1, wherein said substance is a drug or drug precursor.

3. The process according to claim 1 or 2, wherein said polymer is cross-linked polyvinylpyrrolidone or cross-linked sodium carboxymethylcellulose.

4. The process of claim 1 or 2, wherein said polymer is a combination of two or more water-swellable, water-insoluble polymers.

5. A water-swellable, water-insoluble polymer loaded with a biologically active substance or substance convertible into a biologically active substance in vivo in a weight ratio of the said substance:polymer of from 1:0.1 to 1:100 prepared by the process of claim 1 or 2.

6. A pharmaceutical composition, comprising:
   a water-swellable, water-insoluble polymer loaded with a biologically active substance or substance convertible into a biologically active substance in vivo prepared by the process as claimed in claim 1 or 2.

7. The composition according to claim 6 further comprising a pharmaceutically acceptable excipient.

* * * * *